(12) United States Patent
Toure et al.

(10) Patent No.: US 10,835,337 B2
(45) Date of Patent: Nov. 17, 2020

(54) STERILE IMAGING PROTECTIVE SYSTEM

(71) Applicant: TIDI Products, LLC, Neenah, WI (US)

(72) Inventors: Samba Toure, Grand Blanc, MI (US); James Richard Bemman, Holly, MI (US); Nicholas Sievers, Clarkston, MI (US); Eva Elaine Miller, Lexington, KY (US); Brian L. Wilt, Appleton, WI (US)

(73) Assignee: TIDI Products, LLC, Neenah, WI (US)

( * ) Notice: Subject to any disclaimer, the term of this patent is extended or adjusted under 35 U.S.C. 154(b) by 817 days.

(21) Appl. No.: 15/423,204

(22) Filed: Feb. 2, 2017

(65) Prior Publication Data

US 2018/0214228 A1    Aug. 2, 2018

(51) Int. Cl.
*A61B 46/10* (2016.01)
*A61B 46/20* (2016.01)
*A61B 6/00* (2006.01)

(52) U.S. Cl.
CPC ............ *A61B 46/10* (2016.02); *A61B 6/4423* (2013.01); *A61B 6/4441* (2013.01); *A61B 6/487* (2013.01); *A61B 46/20* (2016.02); *A61B 2046/205* (2016.02)

(58) Field of Classification Search
CPC ....... A61B 46/10; A61B 46/23; A61B 6/4441; A61B 6/4452; A61B 6/4423; A61B 6/4405; A61B 46/20; A61B 46/40; A61B 2046/201; A61B 2046/205; A61B 2046/236
See application file for complete search history.

(56) References Cited

U.S. PATENT DOCUMENTS

| | | | |
|---|---|---|---|
| 3,791,382 | A | 2/1974 | Collins |
| 4,489,720 | A | 12/1984 | Morris et al. |
| 4,598,458 | A | 7/1986 | McAllester |
| 4,730,609 | A | 3/1988 | McConnell |
| 5,426,683 | A | 6/1995 | O'Farrell, Jr. et al. |
| 5,445,165 | A | 8/1995 | Fenwick |
| 5,490,524 | A | 2/1996 | Williams et al. |
| 7,044,132 | B2 | 5/2006 | Masini |

(Continued)

FOREIGN PATENT DOCUMENTS

| | | |
|---|---|---|
| WO | WO1996038096 | 12/1996 |
| WO | WO2006038096 | 4/2006 |
| WO | WO2007041093 | 4/2007 |

*Primary Examiner* — Kari K Rodriquez (57) ABSTRACT

Systems and methods for a sterile imaging protective system are described. The system preferably includes a first flexible drape with a cavity configured to surround an imaging intensifier and a second drape that is attached to an operating table or patient drape. The second drape has a proximal portion, a distal portion, a pocket therebetween with a top sterile portion and a lower portion, and a plurality of reusable fasteners that allows the second drape to be repeatedly moved from a collapsed configuration to an expanded configuration. When in the expanded configuration, the second drape is releasably attached to the first drape. The system may also include a third drape located on the opposite side of the operating table as the second drape. The drapes preferably allow sterility to be maintained during movement of the c-arm imaging system.

10 Claims, 7 Drawing Sheets

(56) References Cited

U.S. PATENT DOCUMENTS

| | | |
|---|---|---|
| 7,114,500 B2 | 10/2006 | Bonutti |
| 7,717,117 B2 | 5/2010 | Duarte |
| 7,727,244 B2 | 6/2010 | Orban, III et al. |
| 8,042,549 B2 * | 10/2011 | Kaska .................... A61B 46/10 128/852 |
| 8,286,637 B2 | 10/2012 | Kaska |
| 2006/0020152 A1 | 1/2006 | Theobald et al. |
| 2006/0076024 A1 | 4/2006 | Duarte |
| 2006/0201521 A1 | 9/2006 | Masini |
| 2008/0006278 A1 | 1/2008 | Henke-Sarmento et al. |
| 2008/0047567 A1 | 2/2008 | Bonutti |
| 2009/0266310 A1 * | 10/2009 | Behme ................. A01K 13/007 119/850 |
| 2011/0214679 A1 | 9/2011 | Chua |
| 2013/0167847 A1 * | 7/2013 | Rogers ..................... A61F 5/37 128/869 |
| 2015/0124941 A1 | 5/2015 | Arterson |
| 2015/0173836 A1 | 6/2015 | Pack et al. |

\* cited by examiner

STERILE IMAGING PROTECTIVE SYSTEM

BACKGROUND OF THE INVENTION

1. Field of the Invention

The present invention relates in general to the field of sterile radiological drapes for use with medical imaging equipment. More particularly, the present invention relates to a sterile drape system for use with a c-arm imaging system.

2. Discussion of the Related Art

Hospital-acquired infections are a growing cause of concern. These infections are estimated to affect about 2 million patients annually and cause an estimated 100,000 deaths. In addition to the loss of life, these infections also create significant costs for the healthcare industry. As a result of these dangers and associated costs, hospitals are taking precautionary measures to increase the safety of patients by maintaining sterility within an operating room. This is beneficial both to patients but also the healthcare industry as a whole.

Traditionally, a series of plastic drapes was used to protect a wound and surrounding areas. These rectangular plastic drapes were typically called "half sheets". Half sheets would be placed onto a patient and hang down toward the floor on either side of an operating table. While use of half sheets is effective during many medical procedures, use of half sheets can be less effective during procedures requiring bulky unsterilized equipment. For example, in spinal and orthopedic surgery, it is often necessary to take radiological images of various parts of the patient's body as the surgery proceeds. This in turn requires the positioning and repositioning of the radiological equipment around the operating table.

The most common piece of radiological equipment is a c-arm fluoroscopy unit. When an image of a patient is taken, the c-arm of the fluoroscopy unit must be inserted beneath and through the opposite side of the operating table. The arm is then raised upward so that it is positioned lateral to the area of the patient to be imaged. As a result, there are two unsterilized ends of the fluoroscopy unit on either side of the operating table. These large unsterilized arms create an immediate contamination hazard to the surgeons and the entire surgical field.

Draping the armatures with conventional half-sheets, particularly as the armatures are moved to various locations during surgery, is a cumbersome process that often requires the use of multiple half sheets. Moreover, there is not a single accepted methodology for draping these pieces of radiological equipment, leading to the use of any number of idiosyncratic and unstandardized methods. Improper draping can result in surgical delay and frequently violates sterile technique, exposing patients to unnecessary risk of infection. Finally, because the equipment in question is typically moved in and out of the surgical field multiple times during surgery, even if the device is properly draped initially, there is no established system for storing the drape in a sterile manner and then systematically redraping the equipment.

A number of the drawbacks experienced with previous draping efforts were largely alleviated with the introduction of the drape described in U.S. Pat. Nos. 8,042,549 and 8,286,637, both of which are incorporated herein by reference in their entirety. These patents disclose a sterile imaging drape with a flexible enclosure with a pocket that can be repeatedly expanded and collapsed to an expanded configuration or a collapsed configuration. While this drape is suitable to maintain sterility about a lower imaging unit, the opposite side of the c-arm still presents sterility risks.

What is needed therefore is a draping system that maintains sterility about both sides of a c-arm imaging system. Further, what is also needed is a draping system that can be used multiple times while the c-arm imaging system is moved to various positions.

SUMMARY AND OBJECTS OF THE INVENTION

By way of summary, the present invention is directed to a sterile imaging protective system with a first flexible drape and a second drape. A primary object of the invention is to maintain a sterile field that is the area above an upper surface of the operating table. A primary object of the invention is to provide a first drape with a cavity configured to surround an imaging intensifier associated with a c-arm imaging system. The first flexible drape can be a bag that is pulled down and loosely attached around the imaging intensifier and at least a portion of the c-arm imaging system. A rubber band and a poly-tie can be used to secure the first flexible drape to the image intensifier.

Another object of the invention is to provide a second drape that includes a flexible enclosure with a proximal portion, a distal portion located opposite the proximal portion, and a pocket disposed between the proximal portion and the distal portion. Additionally, the second drape features a top sterile portion and a lower portion, both of which extend from the proximal portion to the distal portion. The second drape also has a plurality of reusable fasteners configured to be releasably attached to the first flexible drape when in an expanded configuration. The reusable fasteners are located on the proximal portion and the distal portion. Possible reusable fasteners can include adhesives, hooks and loops, snaps, latches, hooks, clamps, clips, and zippers. Additionally, the reusable fasteners can have a plurality of release liners that can be removed, for instance, to expose an adhesive tape. The reusable fasteners associated with the distal portion can have one of a hook or loop fastener that can be removed to uncover an adhesive tape. The second drape is configured to be repeatedly expanded and collapsed to take one of the expanded configuration or a collapsed configuration. The combination of the first flexible drape and second drape allows sterility to be maintained about the imaging intensifier as the c-arm imaging system is rotated. The second drape can be attached to a patient drape, or the second drape can be manufactured with a patient drape. The second drape can also have a cuff at the distal portion, where the cuff is used to move the second drape from the collapsed configuration to the expanded configuration. The cuff is used to maintain sterility by providing a common tool to place an operator's hands during attachment or detachment of the second drape to the first drape. Additionally, the second drape can have an elastic band mounted on each side of the pocket.

In accordance with another aspect of the invention, the sterile imaging protective system can include a third drape. The third drape comprises a flexible enclosure with a proximal edge, a distal edge located opposite the proximal edge, and a pocket disposed between the proximal edge and the distal edge. The third drape also has an upper sterile portion and an inner imaging equipment contacting surface, both of which extend from the proximal edge to the distal edge. Additionally, the third drape has a plurality of reusable fasteners located on the proximal edge and the distal edge to secure the enclosure in a collapsed configuration. Because of the configuration of the third drape, it can be repeatedly expanded and collapsed to take one of an expanded configuration or the collapsed configuration. When in the expanded configuration, the pouch is sufficiently dimensioned such that the enclosure may receive and cover at least a portion of a mobile imaging equipment or emitter beneath the inner imaging equipment contacting surface.

Both the second drape and the third drape can be attached to a patient drape, or the second drape and the third drape can be manufactured with a patient drape. Alternatively, the second drape and the third drape can be attached to an operating table. The use of the first flexible drape, the second drape, and the third drape allows sterility to be maintained as the c-arm imaging system is rotated. More specifically, the second drape can maintain sterility about the imaging intensifier on a first side of the operating table and the third drape maintains sterility where an emitter is rotated to a second side of the operating table.

In accordance with another aspect of the invention, these objects are achieved by providing a method of using a sterile imaging protective system. The method can include installing a first flexible drape about an imaging intensifier associated with a c-arm imaging system. The first flexible drape can then be secured to the imaging intensifier and the c-arm imaging system. A second drape having a pouch and an upper sterile portion can be fastened to a patient drape located on an operating table. This can be achieved by removing a release liner located at the distal portion to expose an adhesive tape for mounting the second drape to the table. The c-arm imaging system is then repositioned and moved toward the operating table. A distal end of the second drape is then pulled away from a proximal portion of the second drape. For instance, the second drape may have a cuff located at the distal portion to move the distal portion away from the proximal portion. Fasteners located on the distal portion of the second drape can then be attached to the first flexible drape. While the c-arm imaging system is moved, for instance by rotating the c-arm imaging system so that the imaging intensifier is located below a top surface of the operating table, sterility is maintained about the imaging intensifier. Additionally, the c-arm imaging system can be rotated as needed for imaging. For instance, the c-arm imaging system can be rotated as needed for imaging.

Next, the distal portion of the second drape can be detached from the first flexible sterile drape. The distal portion is then moved toward the proximal portion, and the distal portion is attached to the proximal portion using a fastener. By engaging a plurality of reusable enclosure fasteners associated with the distal portion and the proximal portion, the second drape is secured in the collapsed configuration where the upper sterile portion of the pouch is folded inwardly such that the upper sterile portion is substantially shielded from external contamination while in an unsterile field below the top surface of the operating table. Thereafter, the c-arm imaging system can be moved away from the operating table. Of course, these steps could be performed in a different order than the way they have been listed here.

In accordance with an aspect of the invention, these objects are achieved by providing a method of manufacturing a sterile imaging protective system. The method can include creating a first flexible drape with a cavity. The first flexible drape is then folded into a compact configuration. A second drape is also created with a proximal portion, a distal portion located opposite the proximal portion, and a pocket disposed between the proximal portion and the distal portion. The second drape can be created with a patient drape. Next, a first fastener is applied to a first side of the proximal portion, a second fastener is applied to a second side of the proximal portion, and a third fastener is applied to the distal portion that is compatible with the second fastener. The third fastener can be created with one of a hook and loop on a first side and an adhesive tape on a second side. The second drape is then also folded into a compact configuration.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

1. System Overview

Intra-operative fluoroscopy for orthopedic procedures frequently involves imaging in the horizontal plane, which requires the lower portion of the c-arm (x-ray tube) imaging system to be rotated from an unsterile zone beneath the table into the sterile field. Because of the mobile nature of the c-arm radiological equipment and the nature of its use, maintaining the sterile field is challenging. Previous methods of draping include methods to protect the integrity of the sterile field, the c-arm imaging system must be draped repeatedly throughout the process. Many previous practices were unstandardized resulting in draping procedures that violate the Association of peri-Operative Registered Nurses (AORN) Standards and Recommended Practices, waste time and material, and pose an increased risk of surgical site infection. For instance, normal practice to prepare a room for surgery is to place sterile drapes on a top of the vertical oriented c-arm image intensifier and c-shaped frame prior to beginning a surgery. These previously-used drapes can include band bags with a clip-on drape attached to the c-shaped frame, a large bag with poly-ties, dome bags, and custom-designed drapes designed to fit the c-arm. However, during movement of the c-arm, the entire c-shaped frame will pass beneath the top surface of the operating room table and sometimes the bottom part of an imaging intensifier drape will pass beneath the top surface of the operating room table and, thus, into the unsterile zone. Once the c-arm imaging system is moved back, the once-sterile imaging intensifier drape and c-shaped frame drape create a sterility breach as the compromised drapes end are rotated until they are over top of the patient and surgical site, thus increasing the risk for surgical site infections.

However, the current invention is superior to these previous designs and alleviates the concerns outlined above. This is achieved by using two sterile disposable equipment covers or drapes in unison to maintain a sterile field for the top portion of a mobile c-arm radiological imaging device. The first drape is a bag that covers the c-arm imaging intensifier and the top portion of the c-shaped frame. An elastic band and at least one poly-tie are used to secure the bag to the c-arm imaging intensifier and the top portion of the c-shaped frame. The second drape is a flexible enclosure with a pocket that is placed on top of and secured to a patient drape by an adhesive strip. The c-arm imaging system is moved to a desired position over the patient. The second drape is opened by placing two hands inside a cuff and lifting upward to open up the pocket. A sterile staff member can then remove release liners located on a distal portion of the second drape to expose adhesive. The second drape is then lifted and the adhesive is pressed/anchored onto the backside of the first drape such that the first drape and second drape are connected. An apron or pouch is formed by connecting the second drape to the first drape. The apron or pouch of this invention maintains sterility by placing a sterile barrier or wall between the patient and the non-sterile side during a horizontal c-arm process, such as lateral imaging. Additionally, this system conforms to AORN guidelines by protecting the sterile field with a pouch when the c-arm imaging system is in a position over an operating table. Another benefit to this system is that it provides sufficient access to the back of the c-arm imaging system allowing a radiation tech to manually rotate the c-arm imaging system during imaging.

Additionally, the second drape can easily be aseptically removed/detached from the first drape when the c-arm is no longer in use by using the cuff and pulling the second drape away from the first drape. The distal portion of the second drape is then reattached to the proximal portion. Once this is complete, for ease of access, the c-arm is moved away from the operating table to the operating table and patient. As such, the second drape can be repeatedly used while maintaining sterile technique.

2. Detailed Description of Preferred Embodiments

Figure 1:
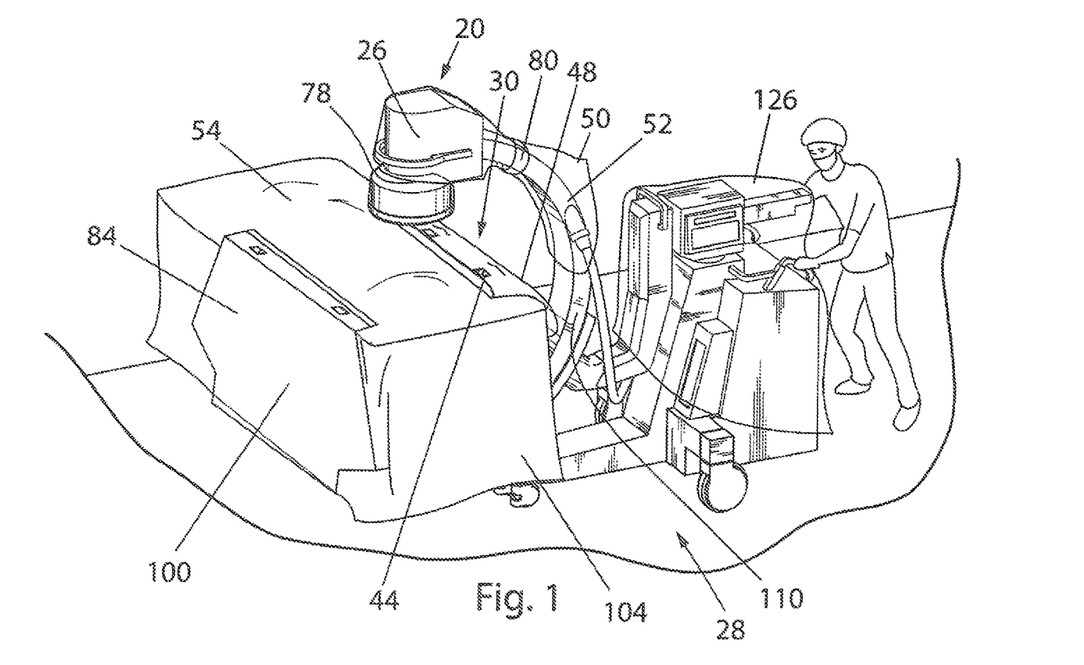
FIG. 1 illustrates a perspective view of an embodiment of the sterile imaging protective system in accordance with the present invention attached to an operating table.

Referring initially to FIG. 1, the inventive sterile imaging protective system 20 for use with a c-arm imaging system 28 is shown. The c-arm imaging system 28 includes an imaging intensifier 26 and an emitter 120 interconnected by a c-shaped frame 110. During operation, the a portion of the imaging intensifier 26 and the c-shaped frame 110 pass beneath the top surface of a surgical operating table 104. The system 20 includes a first drape 22, which is preferably flexible that is positioned about the imaging intensifier 26 and a second drape 30 that is located on or about an operating table 104 or patient drape 54. The system 20 can additionally include a third drape 84 also located on or about the operating table 104 or patient drape 54 configured to maintain sterility about the emitter 120. Each of the first drape 22, second drape 30, and third drape 84 are preferably flexible.

Figure 8:
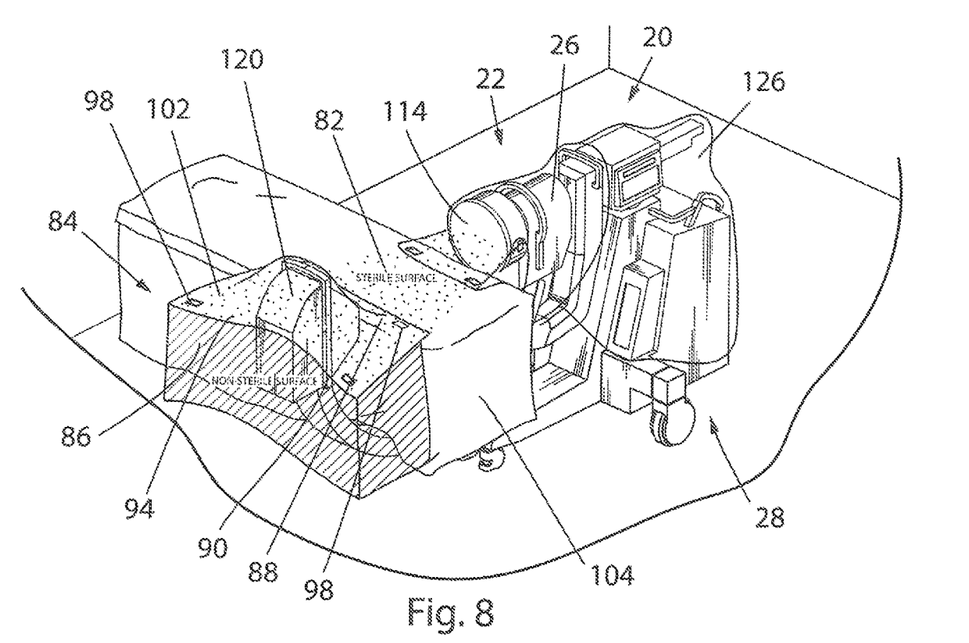
FIG. 8 illustrates a perspective view of the sterile imaging protective system of FIG. 7 with sterile and non-sterile zones.

As will become clear from examination of the illustrations and detailed description, the system 20 of the current invention is designed for use in conjunction with a standard operating table 104 and a traditional patient drape 54 to extend the sterile zone of the surgical environment in a controlled manner. More specifically, as shown in FIG. 8, the surgical environment can be divided into two zones: a sterile area and an unsterile area that are generally defined by the plane formed by the top surface of the operating table 104. The sterile area extends to all equipment positioned on or above the surface of the operating table.

While the below description primarily discusses uses of the sterile imaging protective system 20 with a c-arm imaging system 28, it should be noted that a similar protective system could be used in many other contexts where a drape or a plurality of drapes are used to bridge a gap and maintain sterile technique. For instance, the system 20 could be used to bridge different drapes, to bridge different pieces of medical equipment or tables, or to bridge any other components in order to maintain sterile technique.

Initially, the first flexible drape 22 will be described. As shown, the first flexible drape 22 is a bag 50 with a cavity 24 that is configured to surround the imaging intensifier 26 of the c-arm imaging system 28. However, the first flexible drape 22 could also be a flat sheet that is secured about the imaging intensifier 26. The first drape 22 can be mounted to the c-arm imaging system 28 by slipping the imaging intensifier 26 into the cavity 24 and pulling the first drape 22 down to cover at least a portion of a c-arm frame 110. Once the first drape 22 is pulled down, it can be secured about the imaging intensifier 26 and the c-arm frame 110. This can be accomplished using any number of fasteners. As shown, a rubber band 78 is used to secure the first drape 22 to the imaging intensifier 26 at a ridge found where the imaging intensifier 26 meets the c-arm frame 110. Preferably, the first drape 22 is flush with a bottom surface 114 of the imaging intensifier 26 when the rubber band 78 is applied to optimize operation of the imaging intensifier 26. Additionally, a poly-tie 80 is wrapped around the c-arm frame 110. This helps to ensure the first drape 22 is held closely to the frame 110, which is important so that the first drape 22 does not catch on anything as the c-arm imaging system 28 is rotated.

Figure 2:
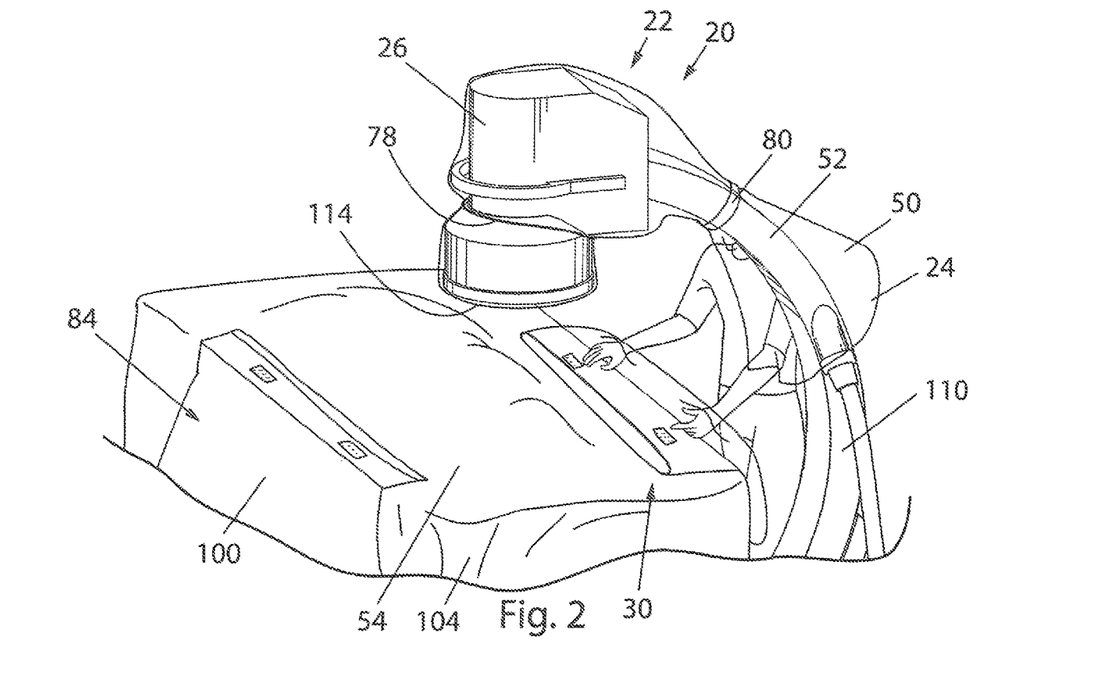
FIG. 2 illustrates a perspective view of the sterile imaging protective system of FIG. 1 where a distal portion of a second drape is separated from a proximal portion using a cuff formed in the distal portion.
Figure 12:
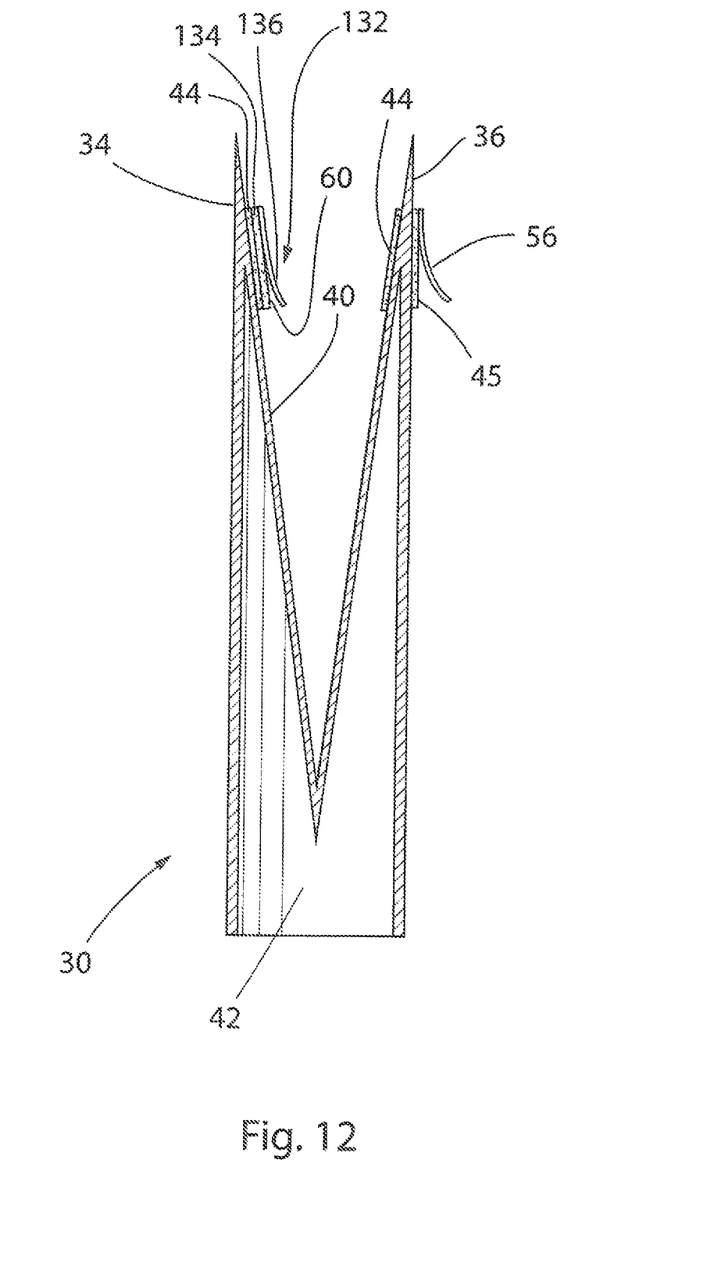
FIG. 12 illustrates a side cross-sectional view of the second drape shown in FIGS. 1-11 before it is installed to the operating table.

Moving now to FIG. 2, the second drape 30 is shown mounted to a patient drape 54. The second drape 30 is a flexible enclosure 32 that includes a distal portion 34 and a proximal portion 36. A pocket 38 is formed between the distal portion 34 and the proximal portion 36. The pocket 38 may be surrounded by an elastic band 76, which encourages the second drape 30 to wrap around a piece of equipment, such as the imaging intensifier 26 thus forming the pocket 38. Additionally, a top sterile portion 40 extends from the distal portion 34 to the proximal portion 36. A lower portion 42 also extends from the distal portion 34 to the proximal portion 36. The proximal portion 36 has a fastener 45 seen in FIG. 12 that is used to secure the second drape 30 to the patient drape 54 or operating table 104. The fastener 45 may be an adhesive tape that is covered by a release liner 56 that can easily be removed when the second drape 30 is attached to the patient drape 54.

Figure 4:
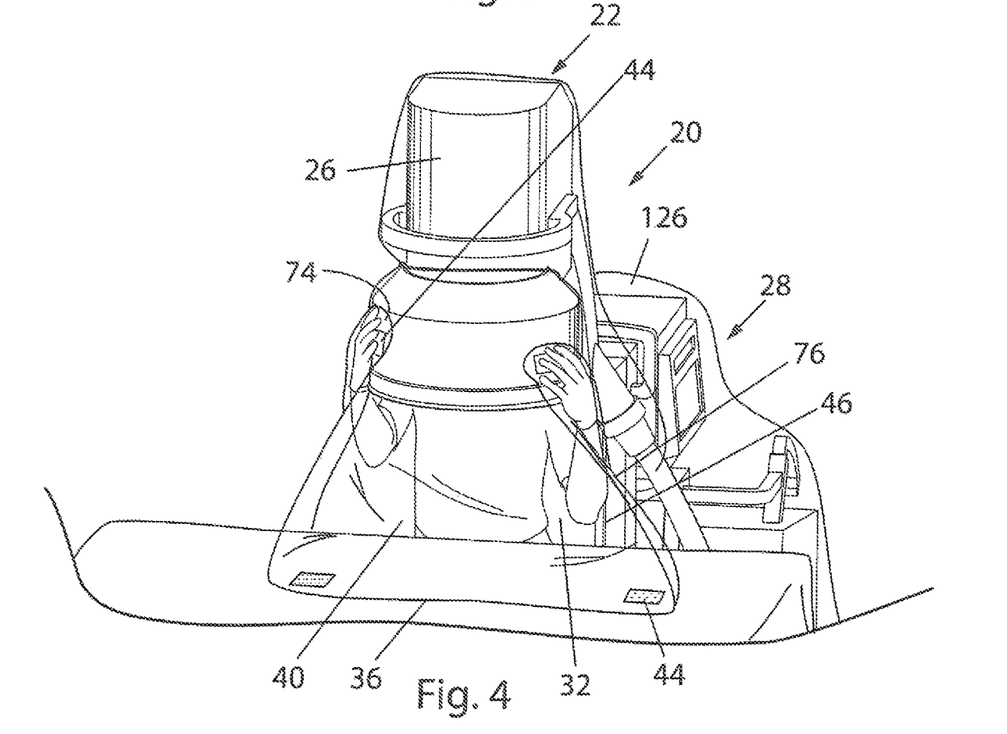
FIG. 4 illustrates a perspective view of the sterile imaging protective system of FIG. 3 where the fastener is attached to a first flexible drape that is covering an imaging intensifier of a c-arm imaging system.

A plurality of reusable fasteners 44 is located along the distal portion 34 and the proximal portion 36. These reusable fasteners 44 can be any fasteners that allow the distal portion 34 to be repeatedly fastened to the proximal portion 36, including but not limited to adhesives, hook and loops, snaps, latches, hooks, clamps, clips, and zippers. As shown in the figures, the reusable fasteners 44 are hook and loop fasteners. The plurality of reusable fasteners 44 allows the second drape 30 to be repeatedly moved from a collapsed configuration 48 to an expanded configuration 46 and back. When in the collapsed configuration 48 as seen for instance in FIG. 1, the top sterile portion 40 is folded inwardly such that the top sterile portion 40 is shielded from external contamination. As a result, the top sterile portion 40 remains sterile. Additionally, the reusable fasteners 44 on the distal portion 34 may have a mounting piece 132 with an adhesive tape 60 on one side and one of a hook and loop fastener 134 on the other side. The hook or loop fastener 134 side of the mounting piece 132 fastens to a portion of the reusable fastener 44 located at the distal portion 34 before the second drape 30 is used. When the second drape 30 is moved to the expanded configuration 46, a release liner 136 covering the adhesive tape 60 can be removed, and the adhesive tape 60 can be fastened to the first drape 22. Thereafter, the reusable fastener 44 of the distal portion 34 can be repeatedly releasably engaged with the hook or loop fastener 134 of the mounting piece 132, as shown in FIG. 4.

Figure 6:
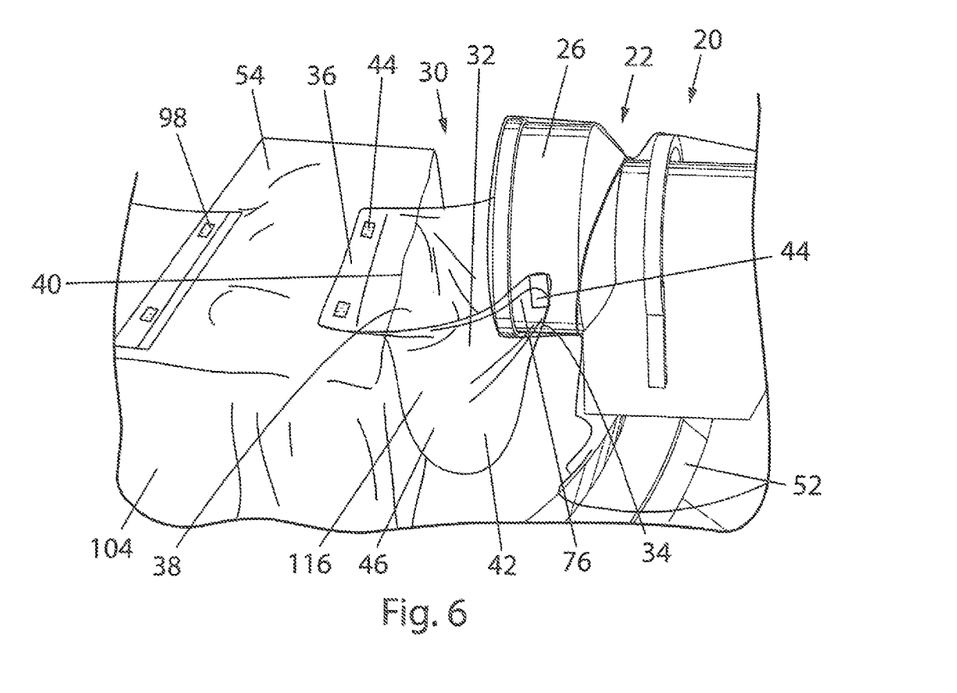
FIG. 6 illustrates a detailed perspective view of the first drape and the second drape of the sterile imaging protective system of FIG. 5 when the c-arm imaging system is substantially horizontal in an angle with an operating table where the c-arm imaging system is in a lateral imaging position.

Once attached, the second drape 30 forms an apron 116 or pouch seen for instance in FIG. 6 that maintains sterility about the imaging intensifier 26 while the c-arm imaging system 28 is rotated by placing a sterile barrier or wall between the patient 118 and the lower portion 42, which is not sterile. Stated differently, sterility is maintained about the imaging intensifier 26 and the portion of the c-arm imaging system 28 even when the imaging intensifier 26 and portion of the c-arm imaging system 28 move beneath the top surface of the operating table 104.

As known to one of ordinary skill in the art, medical procedures often require the c-arm imaging system 28 to initially be used, then moved away from the operating table 104, and then moved back toward the table 104 for additional use. The first drape 22 and second drape 30 allow this all to occur without applying new drapes. Instead, the reusable fastener 44 is simply pulled away from the hook or loop 134 of the mounting piece 132 such that the second drape 30 is detached from the first drape 22. The mounting piece 132 remains attached to the first drape 22 by the adhesive tape 60. The reusable fastener 44 can then be used to releasably attach the proximal portion 36 to the distal portion 34 of the second drape 30 such that the second drape 30 is in a collapsed configuration 48. Once the second drape 30 is returned to the collapsed configuration 48, the c-arm imaging system 28 can be moved away from the operating table 104. A physician can then easily move about the operating table 104 to access the patient 118. In the event that further imaging is required, the c-arm imaging system 28 can be moved toward the operating table 104, and the second drape 30 can be moved to an expanded configuration 102 and releasably attached to the first drape 22. Sterility is maintained while all of this occurs.

Figure 7:
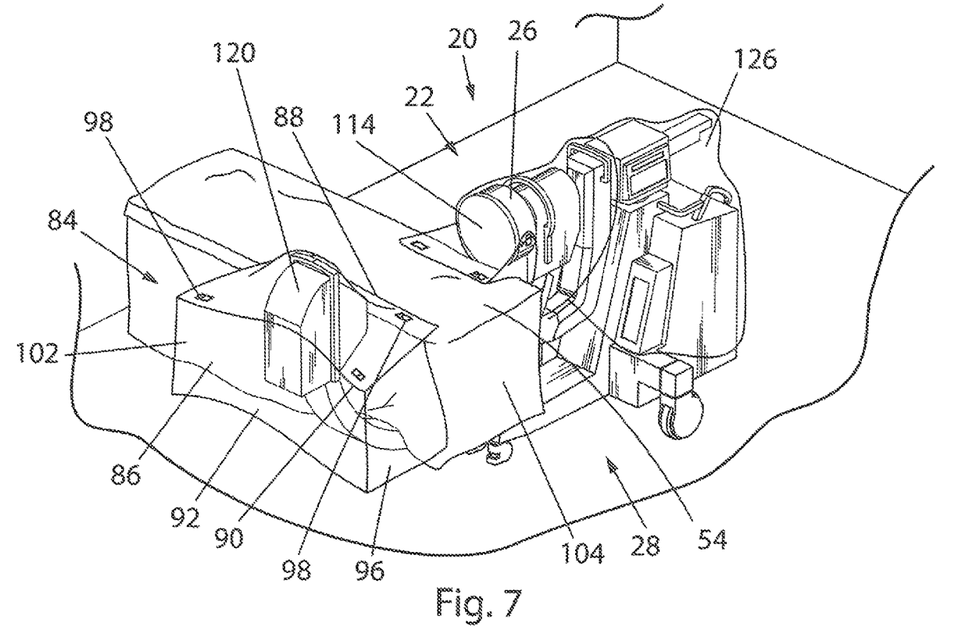
FIG. 7 illustrates a perspective view of the sterile imaging protective system of FIGS. 1-6 where a third drape is shown on an opposite side of the operating table.

Additionally, the system 20 may include a third drape 84, as best seen in FIG. 7. While the third drape 84 will be briefly discussed below, it should be noted that U.S. Pat. Nos. 8,042,549 and 8,286,637, both of which are incorporated herein by reference in their entirety, fully disclose an embodiment of the third drape 84. The third drape 84 is a flexible enclosure with a proximal edge 88, distal edge 90, and a pocket 92 between the proximal edge 88 and the distal edge 90. The third drape 84 also includes an upper sterile portion 94 and an inner imaging equipment contacting surface 96. The proximal edge 88 has a fastener (not shown) that is used to secure the third drape 84 to the patient drape 54 or operating table 104. The fastener (not shown) may be an adhesive tape that is covered by a release liner 124 that can easily be removed when the third drape 84 is attached to the patient drape 54.

As can best be seen in FIGS. 7 and 8, the proximal edge 88 and the distal edge 90 have a plurality of reusable fasteners 98. These reusable fasteners 98 can be any fasteners that allow the proximal edge 88 to be fastened to the distal edge 90, including, but not limited to, adhesives, hook and loops, snaps, latches, hooks, clamps, clips, and zippers. Because of these reusable fasteners 98, the third drape 84 is somewhat similar to the second drape 30 in that it can be moved between a collapsed configuration 100 and an expanded configuration 102 and back. When in the collapsed configuration 100, the upper sterile portion 94 is folded inwardly such that the top sterile portion 40 is shielded from external contamination such that the upper portion 94 remains sterile.

Use of the third drape 84 after the second drape 30 has been attached to the first drape 22 will now be described. The second drape 30 is used with a first side 106 of the operating table 104 and the third drape 84 is used with a second side 108 of the operating table 104. As the c-arm imaging system 28 is rotated downwardly (see FIGS. 5 and 6), the reusable fasteners 98 are disengaged and the distal edge 90 of the third drape 84 is pulled away from the proximal edge 88 so that that the third drape 84 is in the expanded configuration 102. The emitter 120 of the c-arm imaging system 28 located opposite the imaging intensifier 26 enters the pocket 92 such that the inner imaging equipment contacting surface 96 abuts the emitter 120 while sterility is maintained above the operating table 104. When the c-arm imaging system 28 is returned to the first side 106 of the table 104, the distal edge 90 is moved toward the proximal edge 88 such that the upper sterile portion 94 is folded inwardly to substantially shield the sterile upper portion 94 from external contamination once the reusable fasteners 98 are reengaged. In this way, the third drape 84 can be repeatedly expanded to the expanded configuration 102 or collapsed to the collapsed configuration 100 while the c-arm imaging system 28 is continually moved.

Each of the drapes 22, 30, and 84 could be made of any material suitable for use in the sterile environment of an operating theater. For instance, the drapes 22, 30, and 84 could be made of plastic, cloth, paper, synthetics, or a composite of several materials. Additionally, it should be noted that either of the second drape 30 and the third drape 84 could have sidewalls on one or both sides of the respective pocket 38, 92. That said, these drapes 30, 84 could also be formed without sidewalls.

Although the above description describes the first drape 22, second drape 30, and third drape 84 as separate components, it should be noted that any of these drapes or described components could be combined or manufactured together. Similarly, these drapes 22, 30, and 84 or described components thereof could be also be combined with, or manufactured together with, the patient drape 54. Furthermore, each of the drapes 22, 30, and 84 could have additional optional features to enhance the functionality of the system 20.

Further still, the system 20 could include additional drapes to ensure sterility is maintained. For instance, a drape 128 is used with the c-arm imaging system 28 and a drape 126 is affixed to the emitter 120. Again, any of these drapes could be combined or manufactured with the other drapes that have previously been discussed.

Figure 3:
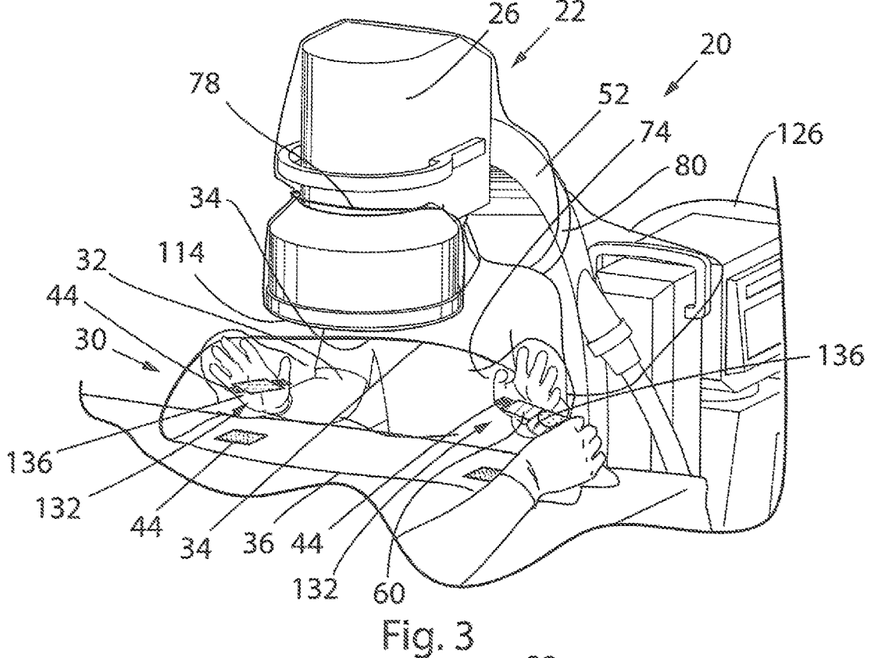
FIG. 3 illustrates a perspective view of the sterile imaging protective system of FIGS. 1 and 2 where a release liner is removed from a fastener located on the distal portion of the second drape.
Figure 5:
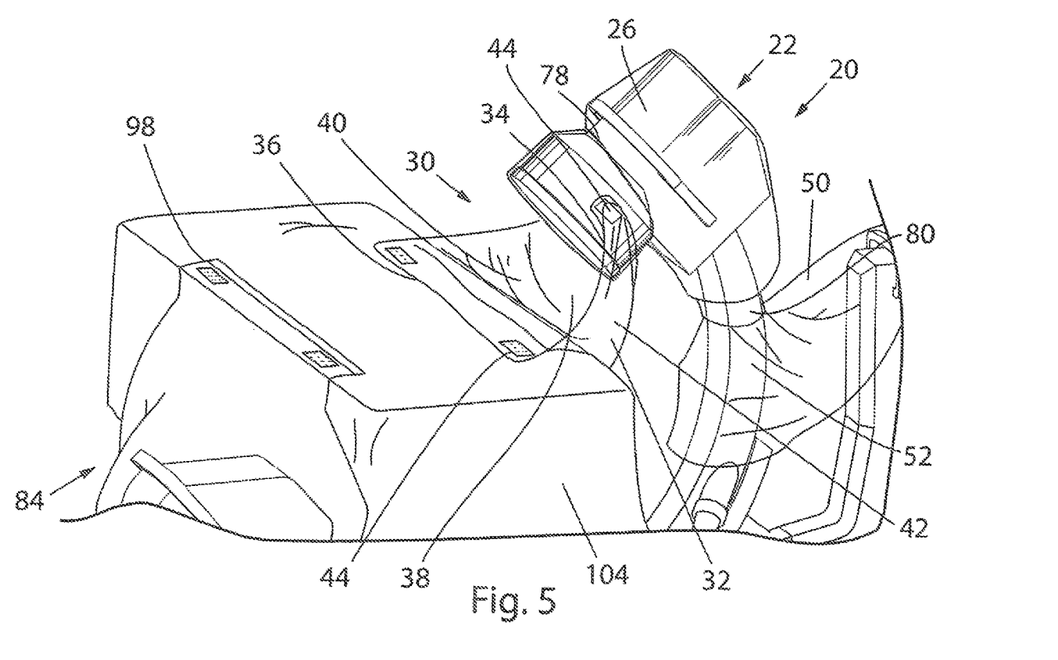
FIG. 5 illustrates a perspective view of the sterile imaging protective system of FIG. 4 where the c-arm imaging system is rotated into an imaging position.
Figure 9:
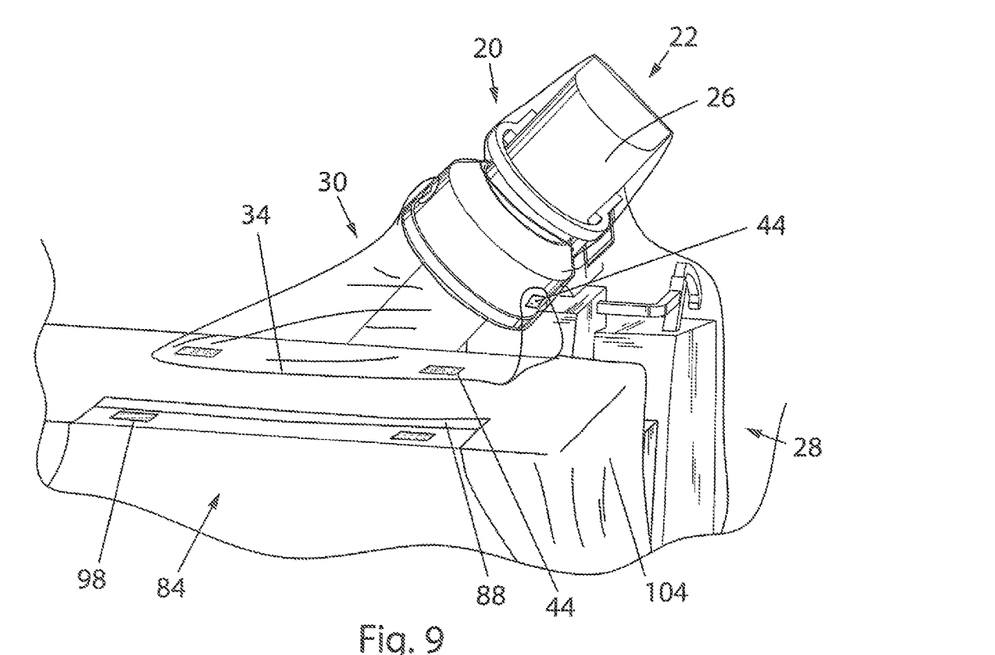
FIG. 9 illustrates a perspective view of the sterile imaging protective system of FIGS. 1-8 where the c-arm imaging system is rotated to a caudle or cranial imaging position.

The present invention is also directed to a method of using the sterile imaging protective system 20, which can include the following steps. First, the first flexible drape 22 is installed about the imaging intensifier 26 associated with the c-arm imaging system 28. Once installed, the first drape 22 is secured to the imaging intensifier 26 and the c-arm imaging system 28. The c-arm imaging system 28 can then be positioned adjacent to the surgical operating table 104 as seen in FIG. 1. Next, the second drape 30 can be attached to the patient drape 54 located on the operating table 104. The distal portion 34 of the second drape 30 is pulled away from the proximal portion 36. For instance, as shown, the second drape 30 may include a cuff 74 located at the distal portion 34 that can be used to pull the distal portion 34 away from the proximal portion 36 as seen in FIG. 2. The second drape 30 is then attached to the first drape 22 using fasteners located on the distal portion 34. For instance, as shown in FIG. 3, a mounting piece 132 with an adhesive tape 60 on one side and one of a hook or loop fastener 134 on the other side may be used to attached the second drape 30 to the first drape 22. Here, a release layer 136 that initially covers the adhesive tape 60 will be removed as shown in FIG. 3 such that the adhesive tape 60 can secure the mounting piece 132 to the second drape 30. Thereafter, the hook or loop fastener 134 can be detached from the reusable fastener 44 of the distal portion 36 of the second drape 30. The reusable fastener 44 at the distal portion 36 of the second drape 30 can then repeatedly be attached to the hook or loop fastener 134 of the mounting piece 132, which remains attached to the first drape 22 by the adhesive tape 60. After the second drape 30 is secured to the first drape 22, the c-arm imaging system 28 can be moved. For instance, as shown in FIGS. 5 and 6, the c-arm imaging system 28 can be moved such that the imaging intensifier 26 is located below a top surface of the operating table 104. Alternatively, as shown in FIG. 9, the c-arm imaging system 28 can be moved to an a caudle or cranial position relative to the operating table 104. During this movement, sterility is maintained about the imaging intensifier 26.

Figure 10:
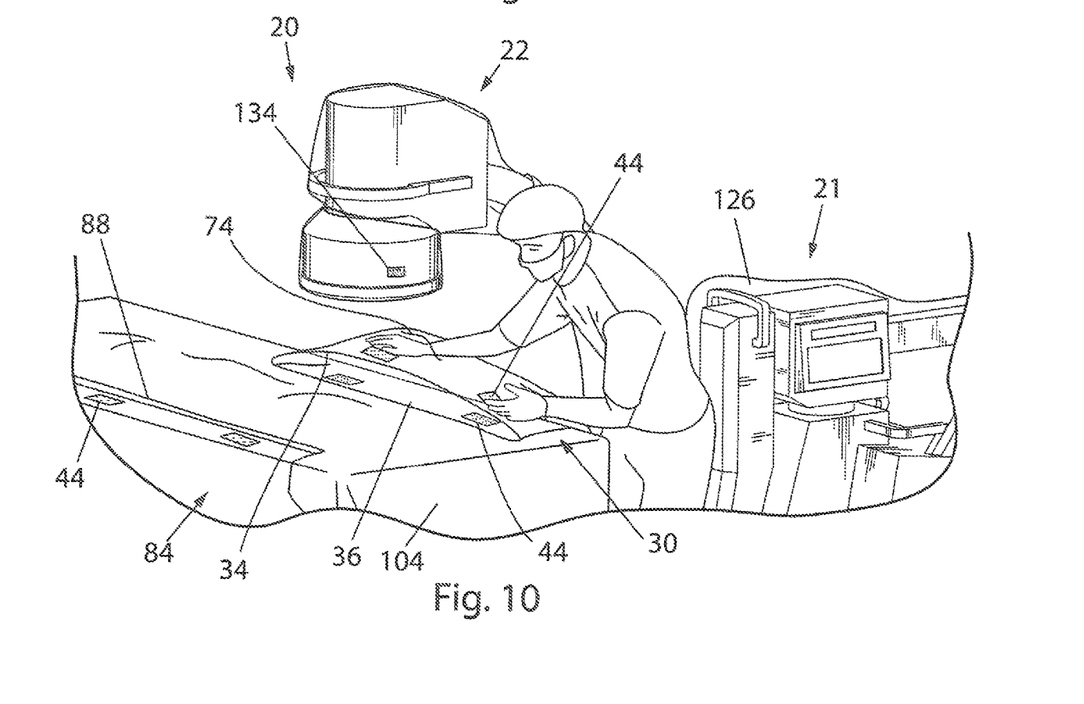
FIG. 10 illustrates a perspective view of the sterile imaging protective system of FIGS. 1-9 where the distal portion of the second drape is detached from the first flexible drape and reattached to the proximal portion.
Figure 11:
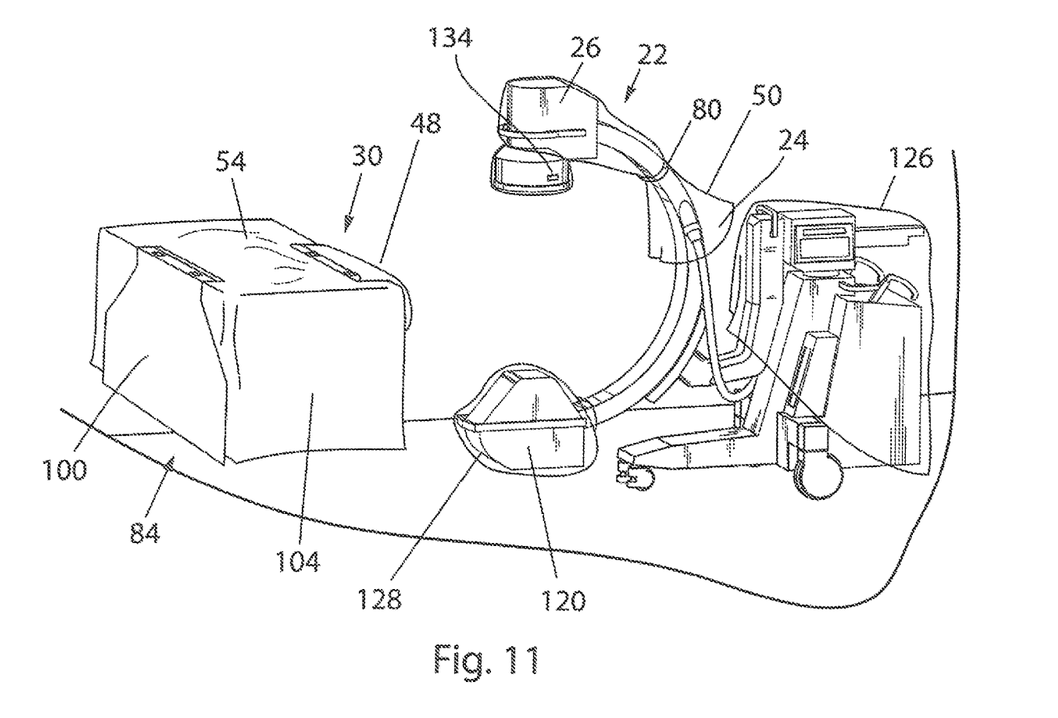
FIG. 11 illustrates a perspective view of the sterile imaging protective system of FIGS. 1-10 where the c-arm imaging system is moved away from the operating table.

Once the imaging procedure has been completed, the distal portion 34 of the second drape 30 can be detached from the first flexible drape 22. The distal portion 34 is then moved toward the proximal portion 36 as seen in FIG. 10 and the proximal portion 36 can be attached to the distal portion 34 using a fastener 44. In doing so, the second drape 30 is secured in a collapsed configuration 48 to fold the top sterile portion 40 of the pocket 38 inwardly such that the top sterile portion 40 is substantially shielded from external contamination while in an unsterile field below the top surface of the operating table 104. Once the second drape 30 has been secured, the c-arm imaging system 28 can be moved away from the operating table 104 as seen in FIG. 11. These steps can be repeated performed several times where multiple images need to be taken.

Additionally, the present invention is also directed to a method of manufacturing the sterile imaging protective system 20. First, a first flexible drape 22 with a cavity 24 is created. Next, the first drape 22 is folded into a compact configuration. A second drape 30 is then created that includes a distal portion 34, a proximal portion 36, and a pocket 38 disposed between the distal portion 34 and the proximal portion 36. A fastener 45 can then applied to a first side of the proximal portion 36. Additionally, second and third fasteners 44 that are compatible with one another can be applied to a second side of the proximal portion 36 and the distal portion 34. For instance, the third fastener 44 can have one of a hook and a loop 58 on a first side and an adhesive tape 60 on a second side. Once assembled, the second drape 30 is folded into a compact configuration. The first drape 22 and the second drape 30 are then packaged together.

Of course, the methods described above could include additional steps. Alternatively, the methods could include some, but not all of, the cited steps. Further still, the methods could include additional steps to improve functionality and sterility of the system 20.

Although the best mode contemplated by the inventors of carrying out the present invention is disclosed above, practice of the present invention is not limited thereto. It will be manifest that various additions, modifications, and rearrangements of the features of the present invention may be made without deviating from the spirit and scope of the underlying inventive concept.

Moreover, the individual components need not be formed in the disclosed shapes, or assembled in the disclosed configuration, but could be provided in virtually any shape and assembled in virtually any configuration. Furthermore, all the disclosed features of each disclosed embodiment can be combined with, or substituted for, the disclosed features of every other disclosed embodiment except where such features are mutually exclusive.

It is intended that the appended claims cover all such additions, modifications, and rearrangements. Expedient embodiments of the present invention are differentiated by the appended claims.

What is claimed is:

1. A sterile imaging protective system for use with an imaging intensifier and c-arm imaging system comprising:
   a first flexible drape with a cavity configured to surround the imaging intensifier associated with the c-arm imaging system; and
   a second drape comprising a flexible enclosure with:
      a proximal portion,
      a distal portion located opposite the proximal portion,
      a pocket disposed between the proximal portion and the distal portion,
      a top sterile portion extending from the proximal portion to the distal portion,
      a lower portion extending from the proximal portion to the distal portion, and
      a plurality of reusable fasteners located on the proximal portion and the distal portion, the plurality of reusable fasteners on the distal portion configured to be releasably attached to the first flexible drape when in an expanded configuration;
   the second drape configured to be repeatedly expanded and collapsed to take one of the expanded configuration or a collapsed configuration;
   a third drape comprising a flexible enclosure with:
      a proximal edge,
      a distal edge located opposite the proximal edge,
      a pocket disposed between the proximal edge and the distal edge,
      an upper sterile portion extending from the proximal edge to the distal edge;
      an inner imaging equipment contacting surface extending from the proximal edge to the distal edge; and
      a plurality of reusable fasteners located on the proximal edge and the distal edge to secure the enclosure in a collapsed configuration;
   the third drape configured to be repeatedly expanded and collapsed to take one of an expanded configuration or the collapsed configuration, wherein the expanded configuration of the pocket is sufficiently dimensioned such that the enclosure may receive and cover at least a portion of a mobile imaging equipment beneath the inner imaging equipment contacting surface;
   wherein the first flexible drape and the second flexible drape are configured to maintain sterility about the imaging intensifier as the c-arm imaging system is rotated; and
   wherein the first flexible drape and the second flexible drape are configured to maintain sterility as the c-arm imaging system is rotated.

2. The sterile imaging protective system of claim 1 wherein the first flexible drape is a bag configured to be pulled down and loosely attached around the imaging intensifier and at least a portion of the c-arm imaging system.

3. The sterile imaging protective system of claim 1 wherein the second drape is attached to a patient drape.

4. The sterile imaging protective system of claim 1 wherein the second drape further comprises a patient drape.

5. The sterile imaging protective system of claim 1 further comprising a mounting piece with an adhesive tape on a first side and one of a hook and loop fastener on a second side, where the adhesive tape secures the mounting piece to the first flexible drape.

6. The sterile imaging protective system of claim 1 wherein the second drape has a cuff at the distal portion, and wherein the cuff is configured to expand the second drape from the collapsed configuration to the expanded configuration.

7. The sterile imaging protective system of claim 1 further comprising an elastic band mounted around the pocket.

8. The sterile imaging protective system of claim 1 wherein the first flexible drape is configured to be secured to the imaging intensifier by a rubber band and poly-tie.

9. The sterile imaging protective system of claim 1 wherein the sterile field is an area above the upper surface of an operating table.

10. The sterile imaging protective system of claim 1 wherein the second drape is configured to maintain sterility about the imaging intensifier on a first side of an operating table and the third drape maintains sterility where an emitter is rotated to a second side of the operating table.

* * * * *